US007883617B2

United States Patent
Einaga et al.

(10) Patent No.: US 7,883,617 B2
(45) Date of Patent: Feb. 8, 2011

(54) ELECTROCHEMICAL ANALYSIS METHOD USING BORON-DOPED ELECTROCONDUCTIVE DIAMOND ELECTRODE

(75) Inventors: Yasuaki Einaga, Yokohama (JP); Daisuke Yamada, Yokohama (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 12/529,130

(22) PCT Filed: Jan. 30, 2008

(86) PCT No.: PCT/JP2008/051413

§ 371 (c)(1),
(2), (4) Date: Sep. 4, 2009

(87) PCT Pub. No.: WO2008/108124

PCT Pub. Date: Sep. 12, 2008

(65) Prior Publication Data

US 2010/0108526 A1 May 6, 2010

(30) Foreign Application Priority Data

Mar. 5, 2007 (JP) .............................. 2007-054284

(51) Int. Cl.
*G01N 27/48* (2006.01)
*G01N 27/30* (2006.01)
(52) U.S. Cl. .................................... 205/789.5; 204/434
(58) Field of Classification Search ................. 204/434; 205/775, 789.5
See application file for complete search history.

(56) References Cited

U.S. PATENT DOCUMENTS 5,571,910 A * 11/1996 Walker et al. ................ 540/230

FOREIGN PATENT DOCUMENTS

| JP | A 6-27081 | 2/1994 |
| JP | A 2006-98281 | 4/2006 |
| JP | A 2006-189400 | 7/2006 |

OTHER PUBLICATIONS

Sun et al, Talanta, 1997, 44(8), pp. 1379-1387.*

* cited by examiner

*Primary Examiner*—Kaj K Olsen
(74) *Attorney, Agent, or Firm*—Oliff & Berridge, PLC

(57) ABSTRACT

This invention provides an electrochemical analysis method for accurately detecting a harmful substance such as arsenic contained in a solution. In the electrochemical analysis method, a working electrode and a counter electrode are disposed in an object electrolytic solution. A negative potential is applied to the working electrode to electrodeposit the electrolyte onto the surface of the working electrode and thus to form an electrodeposit. Next, the potential of the working electrode is swept in a positive potential direction to allow the electrodeposit to elute into the solution and, at the same time, to detect a current change upon a potential change and thus to analyze an object substance dissolved as an electrolyte in the object electrolytic solution. A boron-doped electroconductive diamond electrode or an electrode with gold deposited on its surface is used as the working electrode.

4 Claims, 9 Drawing Sheets

BASE: SILICON PLATE
CARBON SOURCE:
  72 ml ACETONE
  8 ml METHANOL
  $B_2O_3$ 1.09 g
MICROWAVE OUTPUT:
  5000 W
PRESSURE IN CONTAINER:
  110 Torr
REACTION TIME: ABOUT 8 h SEM OF BDD-Au ELECTRODE (a) NITROGEN BUBBLING IS EXHIBITED OR NOT (b) pH INVESTIGATION (c) DIFFERENT ELECTRODEPOSITION TIMES

FIG. 12

(a) PEAK CURRENT VALUES AT DIFFERENT As ELECTRODEPOSITION POTENTIALS

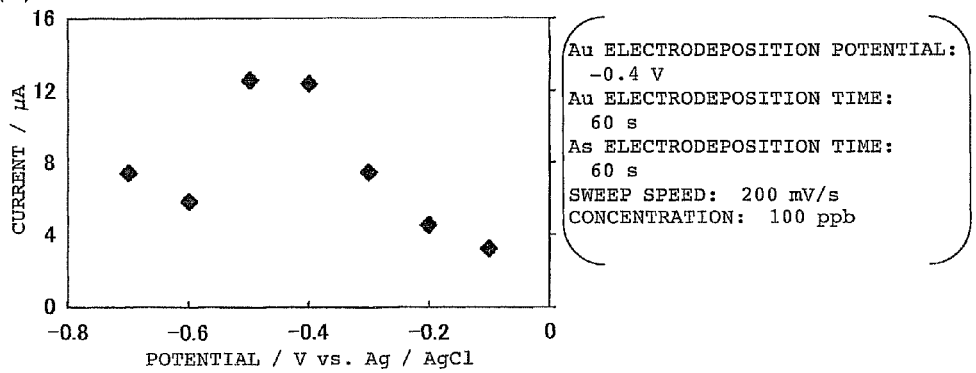

Au ELECTRODEPOSITION POTENTIAL: −0.4 V
Au ELECTRODEPOSITION TIME: 60 s
As ELECTRODEPOSITION TIME: 60 s
SWEEP SPEED: 200 mV/s
CONCENTRATION: 100 ppb (b) PEAK CURRENT VALUES AT DIFFERENT SWEEP SPEEDS

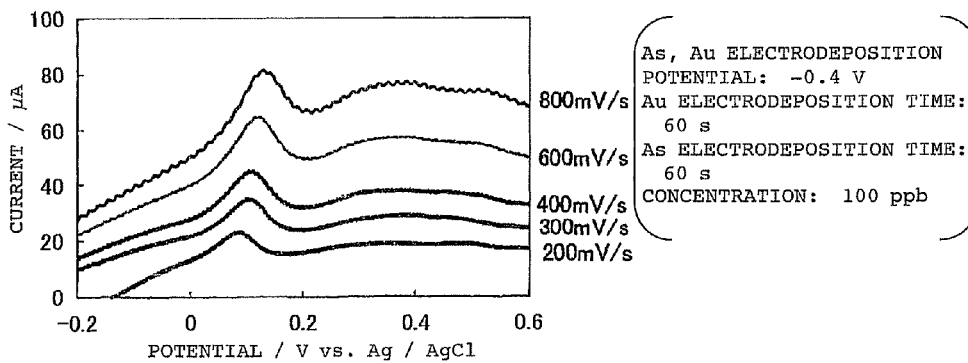

As, Au ELECTRODEPOSITION POTENTIAL: −0.4 V
Au ELECTRODEPOSITION TIME: 60 s
As ELECTRODEPOSITION TIME: 60 s
CONCENTRATION: 100 ppb (c) BACKGROUND AT DIFFERENT Au ELECTRODEPOSITION TIMES

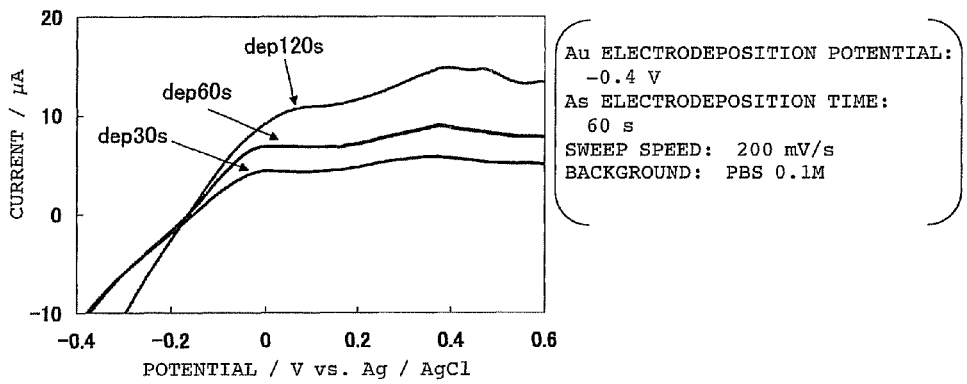

Au ELECTRODEPOSITION POTENTIAL: −0.4 V
As ELECTRODEPOSITION TIME: 60 s
SWEEP SPEED: 200 mV/s
BACKGROUND: PBS 0.1M

ELECTROCHEMICAL ANALYSIS METHOD USING BORON-DOPED ELECTROCONDUCTIVE DIAMOND ELECTRODE

This application is a 371 U.S. National Stage of PCT/JP2008/051413, filed Jan. 30, 2008.

TECHNICAL FIELD

The present invention relates to an analysis method by which an electrochemically active substance in a solution can be analyzed with great accuracy and sensitivity by an electrochemical measurement method using an electroconductive diamond electrode.

BACKGROUND ART

The amounts of harmful substances contained in drinking water and wastewater are strictly regulated, and there is a need for techniques to measure harmful trace metals and other harmful substances in solution with maximum accuracy.

Of the harmful substances, arsenic (As) in particular is an element that easily enters the human body via drinking water and food, and is extremely harmful to humans because it accumulates in the body, causing arsenic poisoning and even death.

For example, arsenic from minerals may seep into ground water, and be ingested by humans as drinking water. Moreover, arsenic may be contained in the wastewater from arsenic mines, where arsenic-containing minerals are mined and used to manufacture arsenous anhydride, and from zinc smelters, where arsine ($AsH_3$) is produced in the cadmium removal purification process when reducing and collecting cadmium. Waste material containing arsenic compounds is also produced by semiconductor plants, in which gallium arsenide (GaAs) and iridium arsenide (IrAs) are used, and arsenous anhydride is also sometimes used as a clarifying agent in the process of manufacturing specialty glass such as optical class, electric glass and the like. At certain times, arsenic compounds are also used as wood preservatives and termite poisons.

The effect on society is severe when such arsenic and arsenic compounds contaminate household water. There is a need for methods whereby arsenic and arsenic compound concentration can be easily and accurately detected not only in drinking water but also in all household water. A spectrophotometric method such as a molybdenum blue method is known as a method for analyzing metal (electrochemical substances) in a solution.

The molybdenum blue method is capable of analyzing arsenic and the like by an easy process that does not require expensive equipment, but it cannot easily detect trace quantities.

Trace substances can be accurately detected by the HPLC-ICP/MS method, which combines high performance liquid chromatography (HPLC) with inductively coupled plasma mass spectroscopy (ICP/MS), but this is a specialized method that can only be performed at certain facilities and requires complicated operations.

By contrast, electrochemical measurement allows trace substances to be detected with easy operations, and also allows quantitative measurement.

One method of electrochemical measurement is the method commonly called "stripping voltammetry".

An outline of this method is explained based on the system illustrated in FIG. 1. An electrolyte solution 1a containing a substance to be measured (such as metal ions) is placed in measurement container 1, which is sealed with seal member 1b. Working electrode 2 and counter-electrode 3 are immersed at a fixed distance from each other in electrolyte solution 1a in measurement container 1. Reference electrode (standard electrode) 5, which is a saturated calomel electrode or the like, is electrically connected to working electrode 2 via capillary 5a, and is also connected to potentiostat 4 via wiring 5b. Potential sweeper 4a and recorder 4b are also connected to potentiostat 4.

When a metal is analyzed in solution, the potential of working electrode 2 is swept from natural electrode potential toward negative potential by potentiostat 4 so that the metal ions in electrolyte solution 1a are electrodeposited one by one on the surface of working electrode 2 to thereby form an electrodeposit (reductive concentration). The potential of the aforementioned working electrode 2 is then swept in the positive direction by means of potentiostat 4 to thereby oxidize and elute the electrodeposit in electrolyte solution 1a. Because each of the metals in the electrodeposit is eluted at a specific oxidation potential, the metal components in electrolyte solution 1a can be analyzed by detecting current changes in response to potential changes at working electrode 2 (peak current relative to potential) when each of the metals is eluted in electrolyte solution 1a (anodestripping).

Patent Document 1 discloses an analysis method using stripping voltammetry, and discloses using a mercury electrode, carbon electrode, mercury-modified carbon electrode, gold-amalgam electrode or the like as the working electrode in this method.

However, accurate analysis of trace quantities has not been achieved with these electrodes due to such problems as low potential windows, heavy background current and the like.

Patent Document 1: Japanese Patent Application Laid-open No. H6-27081

DISCLOSURE OF THE INVENTION

It is an object of the present invention to provide an electrochemical analysis method and system for detecting concentrations of arsenic and other harmful substances in solution with maximum accuracy.

The inventors in this case completed the present invention as a result of exhaustive research when they discovered that the aforementioned problems could be resolved by using a boron-doped electroconductive diamond electrode, or such a diamond electrode with a precious metal attached the surface thereof, as the working electrode in stripping voltammetry.

That is, the present invention comprises the electrochemical analysis method and system described below.

(1) An electrochemical analysis method in which a working electrode and counter-electrode are arranged in an electrolyte solution to be measured, negative potential is applied to the working electrode so that electrolytes are electrodeposited on the surface of the working electrode to form an electrodeposit, and the potential of the working electrode is then swept towards positive potential to thereby elute the electrodeposit in the solution while electric current changes in response to the potential changes are detected to thereby analyze a substance to be measured which is dissolved as an electrolyte in the electrolyte solution to be measured, the method being characterized in that a boron-doped electroconductive diamond electrode is used as the working electrode.

(2) The electrochemical analysis method according to (1) above, characterized in that the diamond of the electroconductive diamond electrode is a vapor-phase synthetic diamond.

(3) The electrochemical analysis method according to (1) or (2) above, characterized in that the electroconductive diamond electrode comprises at least one kind selected from the group consisting of gold, platinum, silver, palladium, ruthenium, rhodium and iridium attached to the surface of the electroconductive diamond.

(4) The electrochemical analysis method according to (3) above, characterized in that the metal attached to the surface of the electroconductive diamond is gold.

(5) The electrochemical analysis method according to (1) or (2) above, characterized in that the electroconductive diamond electrode comprises at least one element selected from the group consisting of gold, platinum, silver, palladium, ruthenium, rhodium and iridium ion-implanted on the surface of an electroconductive diamond.

(6) The electrochemical analysis method according to any of (1) to (5) above, characterized in that when electrodepositing electrolytes on the working electrode, negative potential that electrodeposits only specific electrolytes including a substance to be measured is applied.

(7) The electrochemical analysis method according to any of (1) to (6) above, characterized in that the substance to be measured is arsenic.

(8) The electrochemical analysis method according to (7) above, characterized in that the time for forming the electrodeposit is 3 to 6 minutes, and pH of the solution is 4.5 to 5.5.

(9) The electrochemical analysis method according to any of (1) to (6) above, characterized in that the electrolyte solution to be measured contains electrolytes including an element (M) in a low-oxidation state (M1) and electrolytes including the element in a high-oxidation state (M2), and negative potential that deposits the low-oxidation element (M1) is applied to thereby electrodeposit element (M1) on the working electrode, after which the potential is swept towards positive potential to thereby elute element (M1), and the low-oxidation element (M1) is analyzed.

(10) The electrochemical analysis method according to any of (1) to (6) above, characterized in that the electrolyte solution to be measured contains electrolytes including an element (M) in a low-oxidation state (M1) and electrolytes including the element in a high-oxidation state (M2), and negative potential that deposits the high-oxidation element (M2) on the working electrode is applied to thereby cause an electrodeposition reaction, after which the potential of the working electrode is maintained at the M1 electrodeposition potential and then swept towards positive potential to thereby elute element (M) in the form of the low-oxidation element (M1) as current changes in response to potential changes are detected to thereby analyze element (M).

(11) An electrochemical analysis method in which the analysis value for the high-oxidation element (M2) is obtained from the analysis value for the low-oxidation element (M1) obtained by the method described in (9) above and the analysis value for the element (M) obtained by the method described in (10) above.

(12) The electrochemical analysis method according to any of (9) to (11) above, characterized in that the element (M) is arsenic (As), the low-oxidation element is As(III) and the high-oxidation element is As(V).

(13) The electrochemical analysis method according to any of (1) to (12) above, characterized in that the concentration of the substance to be measured contained in the electrolyte solution to be measured is determined by comparison with a previously-prepared calibration curve of peak current values.

(14) An electrochemical analysis device having a working electrode and a counter-electrode immersed in or in contact with an electrolyte solution to be measured, voltage application means for applying voltage between the working electrode and the counter-electrode, and current measurement means for measuring current flowing between the two electrodes, the electrochemical analysis device being characterized in that a boron-doped electroconductive electrode is used as the working electrode, the electrochemical analysis device further comprising a control unit that operates so that negative potential is supplied to the working electrode and the aforementioned electrolytes are electrodeposited on the surface of the working electrode to form an electrodeposit, after which the potential of the working electrode is swept towards positive potential so as to elute the electrodeposit in the solution, while current changes in response to potential changes are detected to thereby analyze a substance to be measured which is dissolved as an electrolyte in the electrolyte solution to be measured.

(15) The electrochemical analysis device according to (14) above, characterized in that the diamond of the electroconductive diamond electrode is a vapor-phase synthetic diamond.

(16) The electrochemical analysis device according to (14) or (15) above, characterized in that the electroconductive diamond electrode comprises at least one kind selected from the group consisting of gold, platinum, silver, palladium, ruthenium, rhodium and iridium attached to the surface of an electroconductive diamond.

(17) The electrochemical analysis device according to (16) above, characterized in that the metal attached to the surface of the electroconductive diamond is gold.

(18) The electrochemical analysis system according to (14) or (15) above, characterized in that the electroconductive diamond electrode comprises at least one element selected from the group consisting of gold, platinum, silver, palladium, ruthenium, rhodium and iridium ion-implanted on the surface of an electroconductive diamond.

(1) to (18) above are hereunder called embodiments (1) to (18) of the invention.

A trace amount of arsenic or the like contained in a solution can be easily analyzed quantitatively and with maximum accuracy by the method of the present invention.

BRIEF DESCRIPTION OF THE DRAWINGS

FIGS. 12(a), 12(b) and 12(c) show the results of a test used to investigate optimal conditions in Embodiment 4.

EXPLANATION OF REFERENCE NUMERALS

Figure 1:
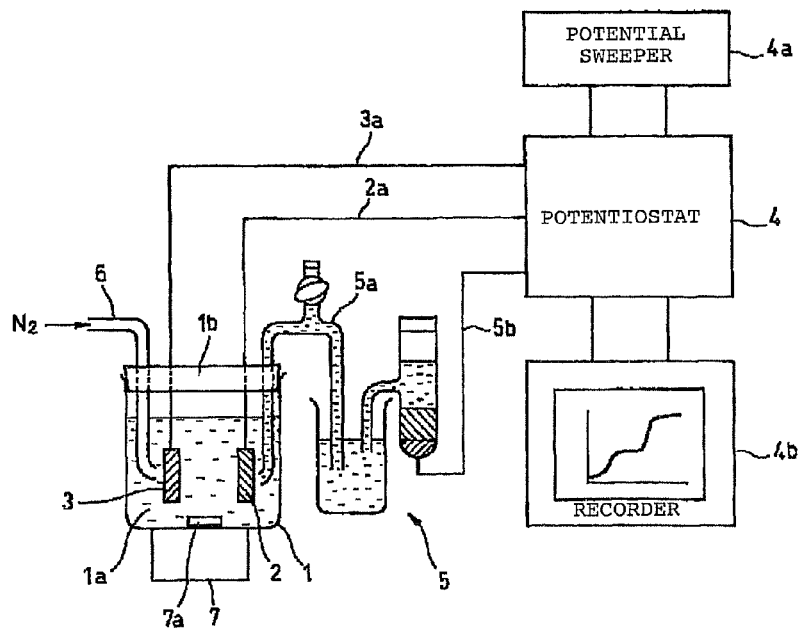
FIG. 1 is a schematic view of a device used in stripping voltammetry.

| | |
|---|---|
| 1 | Measurement container |
| 1a | Electrolyte solution |
| 1b | Seal member |
| 2 | Working electrode |
| 2a | Wiring |
| 3 | Counter-electrode |
| 3a | Wiring |
| 4 | Potentiostat |
| 4a | Potential sweeper |
| 4b | Recorder |
| 5 | Reference electrode |
| 5a | Capillary |
| 5b | Wiring |
| 6 | Supply tube |
| 7 | Stirrer |
| 7a | Agitator |

BEST MODE FOR CARRYING OUT THE INVENTION

The basic principles of the electrochemical analysis method of the present method are those described above as stripping voltammetry. That is, a working electrode and a counter-electrode are arranged in an electrolyte solution containing a substance to be measured (electrochemically active substance) which is the object of analysis, negative potential is applied to the working electrode, the electrolytes are electrodeposited on the surface of the working electrode to form an electrodeposit, and the potential of the working electrode is swept towards positive potential to thereby elute the electrodeposit in the solution while at the same time the substance to be measured is analyzed by detecting current changes in response to the potential changes.

One feature of the present invention is that a boron-doped electroconductive diamond electrode is used as the working electrode.

A boron-doped electroconductive diamond (hereunder sometimes called "BDD") electrode is a diamond that has been doped with boron to make it conductive, and methods for manufacturing boron-doped diamonds are well known.

Because this electrode has a wide potential window, a low background current and high chemical resistance, it can be used in electrochemical analysis of an object of analysis even under severe conditions (such as analysis conditions using a potential pulse with a large amplitude).

Because of these features, moreover, a lower concentration of a substance can be analyzed more sensitively using a boron-doped electroconductive diamond electrode than using other kinds of electrodes.

Using carbon electrodes and other electrodes, moreover, a water electrolysis reaction can occur as a competitive reaction to the electrodeposition reaction when a large negative potential is applied during electrodeposition of a substance to be measured, often producing hydrogen that interferes with electrodeposition of the substance to be measured as well as causing deterioration of the electrode, but boron-doped electroconductive diamond electrodes are not liable to such problems even when a large potential is applied.

This means that maximum measurement accuracy is possible even if the substance to be measured is in a high-oxidation state with a high oxidation-reduction potential.

For example, arsenic can be detected accurately and reproducibly even at concentrations of 5 to 25 ppm using this BDD electrode.

However, in the case of arsenic the wastewater standard under the Clean Water Act is 0.1 ppm (100 ppb), and under the WHO standard arsenic in drinking water is 0.01 ppm (10 ppb) or less, hence the aforementioned BDD electrode is inadequate for analysis on the order of parts per billion.

A second feature of the present invention is that it allows analysis on the order of 100 ppb or less or even 10 ppb or less by using, as the working electrode, an electrode comprising a precious metal such as gold, platinum, silver, palladium, iridium or the like attached to the surface of an electroconductive diamond.

The electrode of the present invention comprising the aforementioned precious metal attached to the surface of a boron-doped electroconductive diamond (hereunder called a "BDD-NM" electrode") can be manufactured by a method such as electrodepositing a precious metal element on a boron-doped electroconductive diamond electrode.

The electrodeposited amount of the precious metal is such that the precious metal does not cover the entire surface of the diamond electrode, and patches of the electroconductive diamond are still visible. This serves to preserve the special properties of the electroconductive diamond while promoting an electrode reaction of the substance to be measured. If the precious metal covers the entire surface of the diamond electrode, the diamond electrode will not perform its proper function, and sensitivity will be poor.

The precious metal on the diamond electrode acts catalytically by providing active sites for the electrode reaction, and it is thought that when several such active sites are present the electrode reaction of the substance to be measured is promoted at the active sites of precious metal, thus allowing the substance to be measured to be analyzed even at low concentrations. Gold is desirable as the precious metal because it is less liable to hydrogen adsorption at low potential than platinum, and is more stable than silver.

One problem with ordinary electrodes is that hydrogen gas is produced by water electrolysis even when the electrodeposition potential is less than −1 V, interfering with electrodeposition, but with a BDD-NM electrode no hydrogen gas occurs up to an electrodeposition potential of about −1 V, so a substance to be measured can be measured even if it has a large oxidation-reduction potential.

The analysis method of the present invention using a BDD-NM electrode must be implemented within a potential range at which the electrodeposited precious metal is not desorbed.

A third feature of the present invention is that an electrode comprising at least one element selected from the group consisting of gold, platinum, silver, palladium, ruthenium, rhodium and iridium ion-implanted on the surface of an electroconductive diamond is used as the working electrode. This electrode has a catalytic effect similar to that of the aforementioned electrode comprising a precious metal element such as gold, platinum, silver, palladium, iridium or the like attached to the surface of an electroconductive diamond.

In the ion implantation method, the element is dispersed in elemental form, and is carried near the surface layer of the diamond. It is thus extremely stable and the exposed surface is also greater, producing a more efficient catalytic effect.

Both contamination by the ionized element and energy radiation damage may occur during ion implantation. Heat treatment (annealing) is therefore performed in order to repair radiation damage and remove implanted element contaminating interstitial sites. By means of this annealing, the damaged surface layer is restored to its original crystal structure in accordance with the atomic arrangement of the underlying crystals. The element thus implanted is exposed on the surface and can exert its desired catalytic function.

This at least one element selected from the group consisting of gold, platinum, silver, palladium, ruthenium, rhodium and iridium is ion implanted using known ion implantation equipment and known ion implantation technology. The ions do not need to be implanted deep inside the diamond thin film; these ions merely have to be carried near the surface. Consequently, the energy that accelerates the ions does not have to be very large: 500 keV to 1 MeV is sufficient.

The implanted amount is preferably about 1 to $10 \times 10^{14}/cm^2$. Since this element only performs a catalytic function in the electrochemical oxidation reaction of the substance being tested, and is not itself consumed, this attached amount is sufficient.

A fourth feature of the present invention is that the high-oxidation element can be quantified using a BDD-NM electrode when an element such as arsenic is present in both high-oxidation and low-oxidation states.

The electrodeposition potential of a high-oxidation element may be below −1V, and as described above, analysis is difficult with a normal electrode in this case because hydrogen gas occurs when the electrodeposition potential is below −1V, inhibiting the electrodeposition reaction. By contrast, a high-oxidation element can be measured by using a BDD-NM electrode if care is taken in how the potential is applied.

First, an electrodeposition reaction is performed by applying negative potential to the working electrode so as to electrodeposit the high-oxidation element (M2) in an electrolyte solution to be measured containing electrolytes including the high-oxidation element (M2).

At this stage hydrogen is produced, making it difficult for the high-oxidation element (M2) to be electrodeposited on the working electrode, but once the potential of the working electrode is immediately held at the electrodeposition potential of the low-oxidation element (M1), hydrogen production stops, and the high-oxidation element (M2) is electrodeposited on the working electrode. This is thought to occur because element (M2) is reduced to the state of element (M1) when negative potential is applied so as to electrodeposit element (M2), and is then electrodeposited at the electrodeposition potential of element (M1).

Next, the potential of the working electrode is swept in the positive potential direction to thereby elute the electrodeposited substance in the form of the low-oxidation element (M1), and the current changes in response to this potential change are detected to thereby analyze the high-oxidation element.

A fifth feature of the present invention is that by using a BDD-NM electrode, it is possible to analyze the concentrations of both a low-oxidation element (M1) and a high-oxidation element (M2) in a solution containing electrolytes including the high-oxidation form (M2) and electrolytes including the low-oxidation form (M1) of a specific element (M).

That is, the low-oxidation element (M1) and high-oxidation element (M2) have different oxidation-reduction potentials, with the high-oxidation element (M2) having a high oxidation-reduction potential which may be below −1 V (−1.5 V in the case of As(V)).

In this case, any effort to electrodeposit the high-oxidation element (M2) will be inhibited by hydrogen produced by water hydrolysis when attempting to electrodeposit the high-oxidation element (M2), thus making it difficult to analyze the total amount of element (M).

Using a BDD-NM electrode, on the other hand, element (M1) and element (M2) can each be analyzed quantitatively as described above if care is taken in how the potential is applied as described above.

These operations are described below.

First, an electrolyte solution to be measured containing electrolytes including the high-oxidation form (M2) and electrolytes including the low-oxidation form (M1) of an element (M) is subjected to an electrodeposition reaction by applying negative potential to the working electrode so as to deposit the high-oxidation element (M2).

At this stage hydrogen is produced, making it difficult for the high-oxidation element (M2) to be deposited on the working electrode. However, once the potential of the working electrode is immediately held at the electrodeposition potential of the low-oxidation element (M1), hydrogen production stops, and the high-oxidation element (M2) is electrodeposited on the working electrode. This is thought to occur because element (M2) is reduced to the state of element (M1) when negative potential is applied so as to electrodeposit element (M2), and this is then electrodeposited at the electrodeposition potential of element (M1).

Next, the potential of the working electrode is swept in the positive potential direction to thereby elute the electrodeposited element (M=M1+M2) in the form of the low-oxidation element (M1), and the current changes in response to this potential change are detected to thereby analyze the element (M=M1+M2). This analysis value represents the total amount of element (M).

Meanwhile, negative potential such as to electrodeposit the low-oxidation element (M1) is applied to the working electrode in the same electrolyte solution to be measured to thereby electrodeposit element (M1) on the working electrode, after which the potential is swept in the positive direction to thereby elute the electrodeposited element (M1), and the low-oxidation element (M1) is analyzed. This analysis value represents the amount of element (M1).

The analysis value for element (M2) is then derived from the analysis value for the total amount of element (M) and the analysis value for the element (M1).

These methods are described in detail below as they are used to analyze a solution containing As(III) and As(V).

The standard oxidation potential of As(V) is as follows:

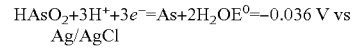

$$As_2O_3 + H_2O = 2HAsO_2$$

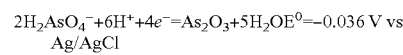

As shown above, electrodeposition of As(V) is more difficult than electrodeposition of As(III) because it requires two stages, a reduction reaction and an electrodeposition reaction.

Thus, −1.5 V of potential is required to electrodeposit As(V).

With an ordinary electrode, a reaction occurs that produces hydrogen gas on the electrode by hydrolysis of water even at −1 V potential or less, inhibiting electrodeposition of As(V) on the electrode and causing the electrode itself to deteriorate if it is a GC electrode.

By contrast, no hydrogen is produced below −1 V with a BBD-Au electrode. Hydrogen does occur at potential of −1.5 V with a BBD-Au electrode as with other electrodes, however, inhibiting electrodeposition of As(V).

At the electrodeposition stage, therefore, the potential is held at the potential of −1.5 V at which As(V) is reduced in the present invention, and then immediately switched to −0.4 V potential and maintained there for a specific time (10 to 30 seconds) to thereby electrodeposit As(V) and As(III) simultaneously on the electrode. After this, the potential is swept in the positive direction to elute the electrodeposit, and the total amount of As(V) and As(III) in the test liquid can be detected as the peak current value of As(III).

The concentration of As(III) in the test liquid can also be quantified by first electrodepositing As (III) with an electrodeposition potential of −0.4 V using the same test liquid, sweeping the potential and then detecting the As(III).

The concentration of As(V) can then be quantified by subtracting the detected value for As(III) from the detected value for total As (As (III)+(As(V)).

This kind of measurement is only possible using a BDD-Au electrode, and cannot be accomplished with any other electrode.

A sixth feature of the present invention is that in an electrochemical analysis system equipped with a working electrode and counter-electrode immersed in or in contact with an electrolyte solution to be measured, a voltage application means for applying voltage between the working electrode and counter-electrode and a current measurement means for measuring current flowing between the two electrodes, the electrochemical analysis system is equipped with a control unit that operates so that the potential of the working electrode is swept in the positive direction so as to elute the electrodeposit in the solution, while at the same time current changes in response to potential changes are detected to thereby analyze a substance to be measured which is dissolved as an electrolyte in the electrolyte solution to be measured. This control unit has software that controls the aforementioned operations, and the analysis operations can be automated by means of this configuration.

A vapor-phase synthetic diamond can be used as the diamond of the electroconductive diamond electrode of the electrochemical analysis system of the present invention, and one may be used that comprises at least one kind selected from the group consisting of gold, platinum, silver, palladium, ruthenium, rhodium and iridium attached to the surface of this electroconductive diamond.

The aforementioned control unit may be provided with a control unit programmed so as to implement the methods of the aforementioned embodiments (8) to (12) of the invention.

EMBODIMENTS

Embodiments of the present invention are given below using arsenic as the substance to be measured, but the present invention is not limited by these embodiments.

The samples used in the embodiments, the methods for manufacturing the electrodes and the equipment used for analysis are discussed first.

(1) Samples

The following samples are used in the embodiments, with the As(III) source and As(V) source used either separately or mixed together as the arsenic source according to the test.

As(III) source: Sodium metaarsenite (III) ($NaAsO_2$)

As(V) source: Disodium hydrogen arsenate (V) ($Na_2HAsO_4$-$7H_2O$)

Solvent: Hydrochloric acid, PBS 0.1 M (2) BDD electrode manufacturing method

Figure 2:
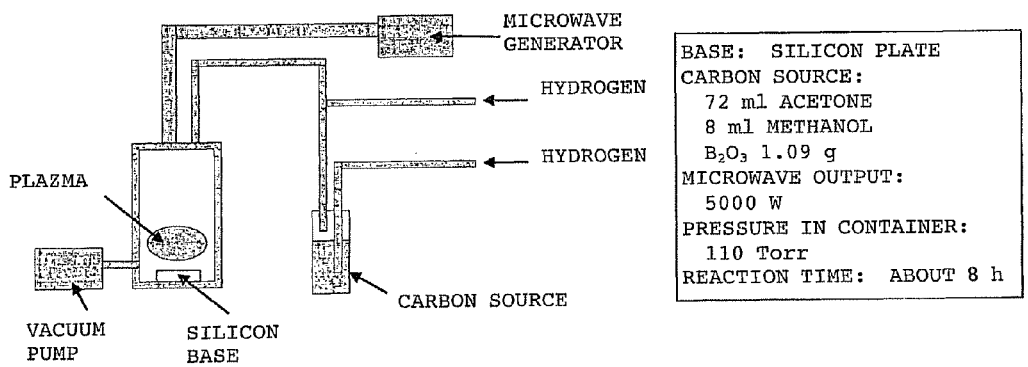
FIG. 2 is a schematic view of a microwave plasma CVD system.

The BDD electrode was made by microwave plasma-assisted CVD as shown below using a microwave CVD deposition system made by ASTeX Co. as the deposition system. An outline of this system is shown in FIG. 2.

A silicon substrate (Si(100)) was used as the electroconductive substrate, and the surface of this silicon substrate was first texture treated (for example, polished with 0.5 μm diamond powder) before being fixed in a holder on the deposition system. A mixture of acetone and methanol (liquid mixing ratio 9:1 by volume) with boron oxide ($B_2O_3$) dissolved therein to a boron/carbon (B/C) ratio of $10^4$ ppm was used as the film-formation source.

Pure $H_2$ gas as a carrier gas was passed through this film-formation source before it was introduced into a chamber. This chamber had been previously adjusted to 115 Torr by passing hydrogen at a flow rate of 532 cc/min through another line. Next, the inside of the chamber was charged with 2.45 GHz of microwave power, and the electric power was adjusted to 5 kW.

Once the power had stabilized, pure $H_2$ gas was supplied as a carrier gas to the film-formation source, and a film was deposited at a film-formation speed of 1 to 4 μm/h. An electroconductive diamond electrode consisting of a roughly 30 μm-thick film (electrode area less than 1 $cm^2$) was obtained after about 8 hours of reaction time. The substrate temperature was about 850 to 950° in a stable state.

(3) Gold-Attached BDD Electrode

A 1 M $K[Au(Cl)_4]$ aqueous solution was diluted 10 times with 0.1 M hydrochloric acid, and this solution was reduced for a specific time by chronoamperometry to electrodeposit the gold and manufacture a gold-attached BDD electrode (hereunder "BDD-Au electrode"). Unless otherwise specified, the gold was electrodeposited by 4 minutes' reduction at −0.4 V in the embodiments using a BDD-Au electrode.

The standard oxidation potential of gold is as follows.

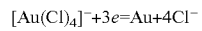

$[Au(Cl)_4]^- + 3e = Au + 4Cl^-$ $E^0 = 0.782$ V vs. Ag/AgCl

Figure 3:
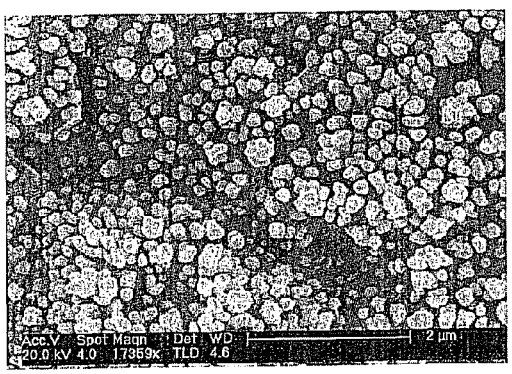
FIG. 3 is an SEM image of the surface of a BDD-Au electrode.

FIG. 3 shows an SEM image of the surface of a BDD-Au electrode obtained by electrodepositing gold by 4 minutes' reduction at −0.4 V. In FIG. 3, the part with deposited gold shows white, while the exposed diamond surfaces show black.

(4) System

Figure 4:
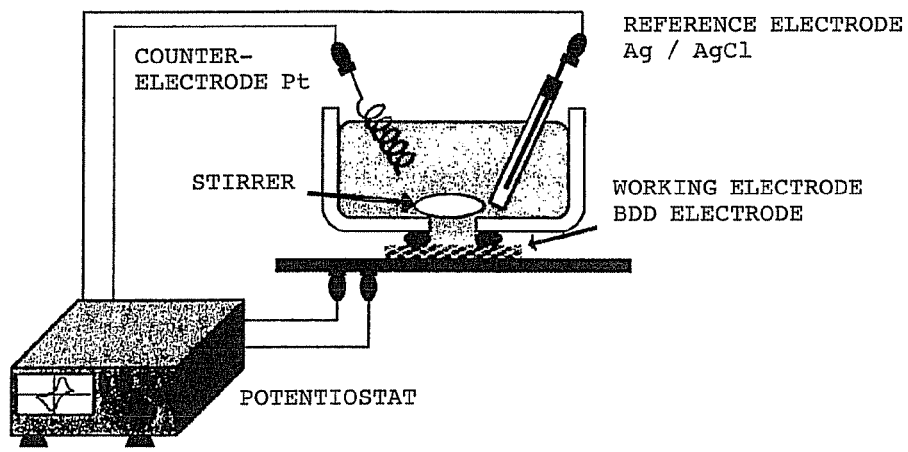
FIG. 4 is a schematic view of an electrochemical analysis system used in the embodiments.

The system shown in outline in FIG. 4 was used. A Pt electrode was used as the counter-electrode and an [Ag/AgCl] electrode as the reference electrode.

Embodiment 1

Measuring As (III) with a BDD Electrode

Using the system shown in FIG. 4, a solution containing arsenic was analyzed in this embodiment using a BDD electrode as the working electrode.

Figure 5:
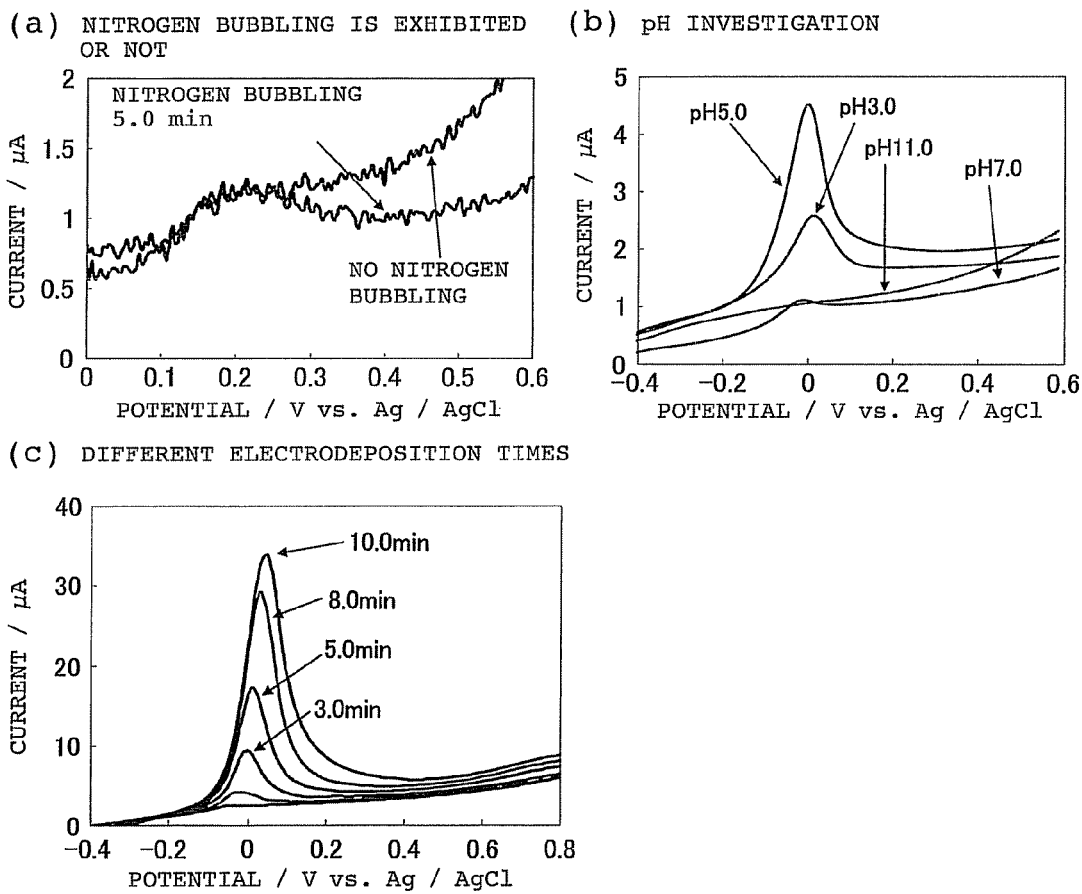
FIGS. 5(a), 5(b) and 5(c) show the results of a test used to investigate optimal conditions in Embodiment 1.

First, the electrodeposition time, solution pH and the like were tested in order to optimize the conditions for analyzing arsenic in a solution prior to testing. The results are shown in FIG. 5.

FIG. 5(a) shows the relationship between nitrogen bubbling and peak current value, while FIG. 5(b) shows the relationship between solution pH and peak current value, and FIG. 5(c) shows the relationship between electrodeposition time and peak current value.

These results showed the following conditions to be desirable, and these conditions were adopted for analysis.

Nitrogen bubbling does not seem to have any particular effect on the analysis results, but was set as follows in order to remove dissolved oxygen.

| | |
|---|---|
| Electrodeposition time: | 5 minutes |
| Solution pH: | 5 |
| Nitrogen bubbling: | 5 minutes |

With the potential of the working electrode at −0.4 V, the arsenic in the aqueous solution was electrodeposited on the working electrode to form an electrodeposit.

The standard oxidation potential of As(III) is as follows.

$HAsO_2 + 3H^+ + 3e^- = As + 2H_2O$ $E^0 = -0.036$ V vs Ag/AgCl (pH 5.0)

Next, the potential of the working electrode was swept in the positive direction to elute the electrodeposit in the solution, and current changes during this time were measured.

Figure 6:
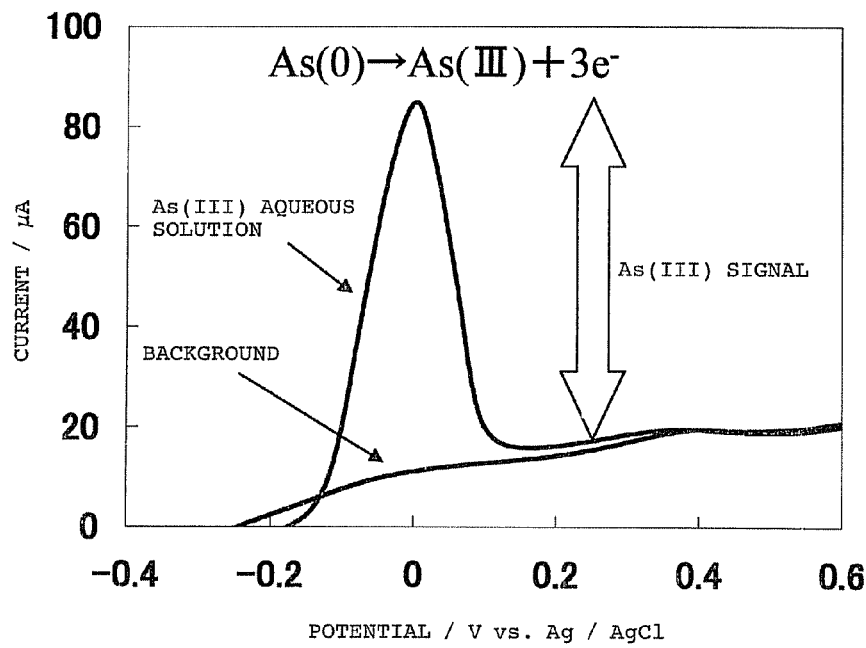
FIG. 6 shows As solution analysis results obtained by measurement using a BDD electrode.

FIG. 6 shows the resulting current curve. It can be seen from this curve that the position of the peak potential roughly matches the position of the standard oxidation potential of arsenic.

Figure 7:
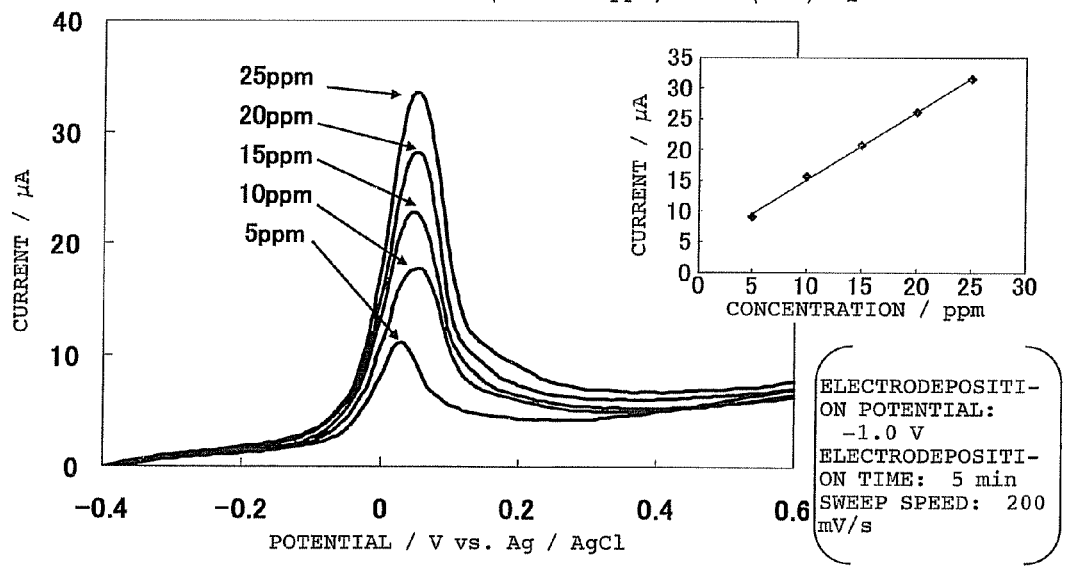
FIG. 7 shows analysis results obtained in Embodiment 1 for As solutions of various concentrations.

Next, similar operations were performed using As aqueous solution of various concentrations (5 ppm, 10 ppm, 15 ppm, 20 ppm, 25 ppm) to obtain current curves, and the relationship between peak current and As concentration was plotted on a graph to prepare a calibration curve. FIG. 7 shows the measurement results for the solutions and the calibration curve prepared based on these measurement results.

In this embodiment it was possible with the method using a BDD electrode of the present invention to detect a peak corresponding to a concentration in the range of 5 to 25 ppm.

Figure 8:
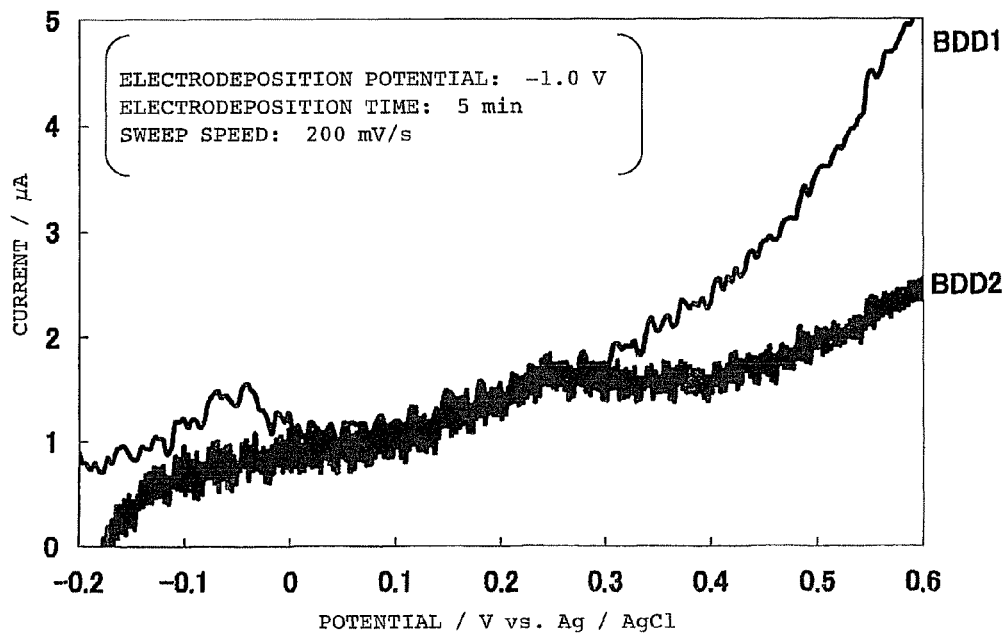
FIG. 8 shows analysis results obtained in Embodiment 1 for a low-concentration (100 ppb) As solution.

When analysis tests were performed for each electrode using two BDD electrodes (BDD1 and BDD2) and a solution with a 100 ppb As concentration, the current curve shown in FIG. 8 was obtained.

It can be seen from this figure that with the system used in this embodiment, although a peak may appear depending on the electrode, reproducibility is poor, and the peak is broad, indicating little electrodeposition of arsenic.

Embodiment 2

Measurement of As(III) Using BDD-Au Electrode

Solutions containing arsenic at low concentrations were analyzed in this embodiment using a BDD-Au electrode as the working electrode.

Figure 9:
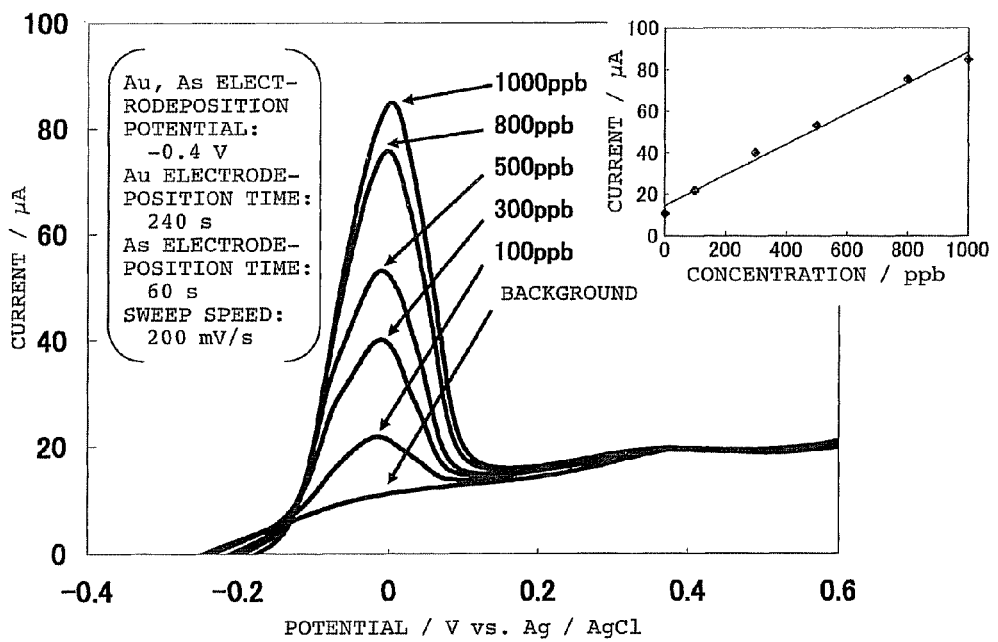
FIG. 9 shows analysis results obtained in Embodiment 2 for As solutions of various concentrations.

Sample solutions containing 100 ppb, 300 ppb, 500 ppb, 800 ppb and 1000 ppb of As(III) were prepared, and the analysis method of the present invention was applied to these sample solutions under the following conditions using a BDD-Au electrode as the working electrode, with the results shown in FIG. 9.

| | |
|---|---|
| As electrodeposition potential: | −0.4 V |
| As electrodeposition time: | 60 s |
| Sweep speed: | 200 mV/s |
| Au electrodeposition time: | 240 s |

It can be seen from this embodiment that a peak corresponding to concentration can be detected even at a low concentration of 100 to 1000 ppb by using a BDD-Au electrode as the working electrode.

Embodiment 3

Measurement of As(III) Using BDD-Au Electrode

In this embodiment, analysis tests were performed as in Embodiment 2 except that the concentrations of the solutions were 10 ppb, 30 ppb, 50 ppb and 100 ppb.

Figure 10:
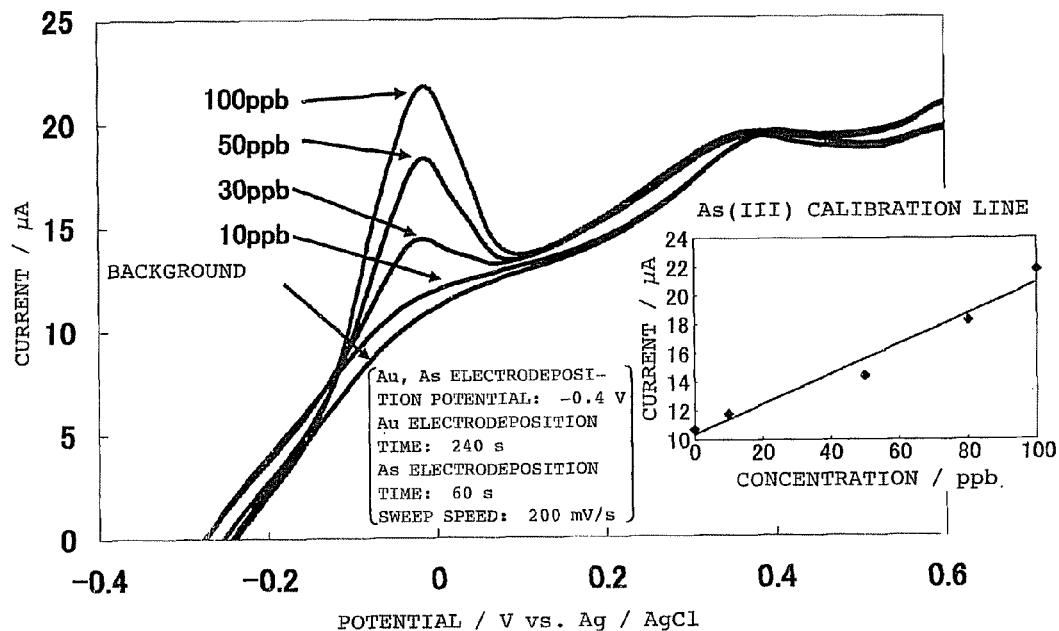
FIG. 10 shows analysis results obtained in Embodiment 3 for As solutions of various concentrations.

The results are shown in FIG. 10.

It can be seen from the results of this embodiment that a peak corresponding to arsenic concentration in a solution can be obtained even at a low concentration of 10 to 100 ppb by using a BDD-Au electrode as the working electrode.

By way of reference, solutions containing 100 ppb of As were analyzed under the same conditions as in this embodiment using a BDD-Au electrode, BDD electrode, Au plate electrode and GC-Au (Au deposited on glassy carbon) electrode as the working electrodes. The results are shown in FIG. 11.

Figure 11:
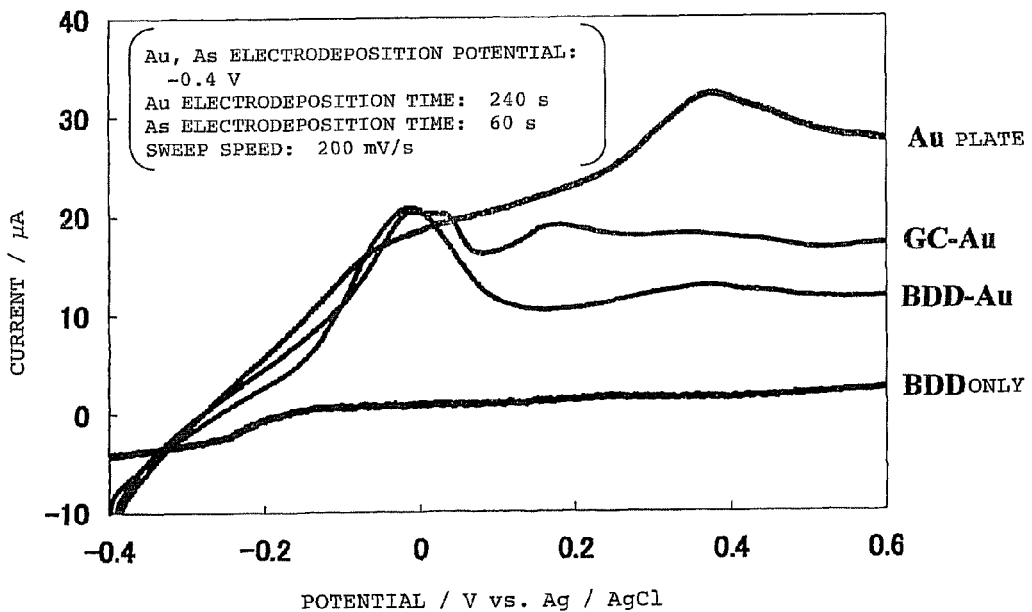
FIG. 11 shows a comparison of the BDD-Au electrode obtained in Embodiment 3 with other electrodes.

It is clear from FIG. 11 that while a clear peak appears using the BDD-Au electrode, no clear peak appears using the other electrodes. This shows that the BDD-Au electrode is especially suited to detecting arsenic at low concentrations.

Embodiment 4

Measurement of As (III) Using BDD-Au Electrode

In this embodiment the optimum conditions for analyzing a solution containing an ultralow concentration (5 ppb or less) of As (III) were investigated, and an ultralow-concentration As solution was analyzed based on the resulting optimum conditions.

First, in order to optimize the analysis conditions, BDD-Au electrode Au electrodeposition times, As electrodeposition potentials and sweep speeds were selected as analysis conditions, and used to test a solution with a 100 ppb As concentration. The results are shown in FIG. 12.

FIG. 12(a) shows the relationship between As electrodeposition potential and peak current value, FIG. 12(b) shows the relationship between sweep speed and peak current value, and FIG. 12(c) shows the relationship between Au electrodeposition time and peak current value.

FIG. 12(a) shows that a high peak current value is obtained when the electrodeposition potential is in the range of −0.4 to −0.5.

FIG. 12(b) shows that a high peak current value is obtained when the sweep speed is 600 mV/s or more.

FIG. 12(c) shows that the background around the As peak potential is flat when the Au electrodeposition time is 1.0 min.

The following conditions were set as optimum conditions based on these results.

| | |
|---|---|
| As electrodeposition potential: | −0.4 V |
| As electrodeposition time: | 60 s |
| Sweep speed: | 600 mV/s |
| Au electrodeposition time: | 1.0 min |

Figure 13:
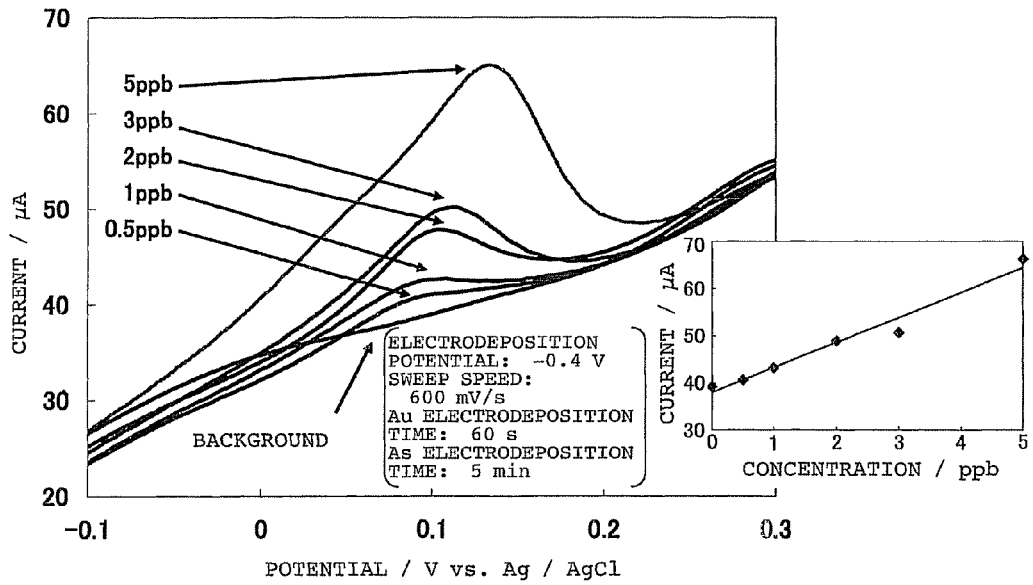
FIG. 13 shows analysis results obtained in Embodiment 4 for an ultralow concentration solution.

Next, sample solutions containing 0.5 ppb, 1 ppb, 2 ppb, 3 ppb and 5 ppb of As(III) were prepared, and these sample solutions were subjected to the analysis method under the aforementioned conditions using a BDD-Au electrode as the working electrode, with the results shown in FIG. 13.

It appears from this embodiment that detection down to 0.5 ppb (500 ppt) can be achieved using a BDD-Au electrode as the working electrode if the conditions are optimized.

Reproducibility was then tested when measuring an As(III) solution with a 10 ppb concentration using a BDD-Au electrode.

Figure 14:
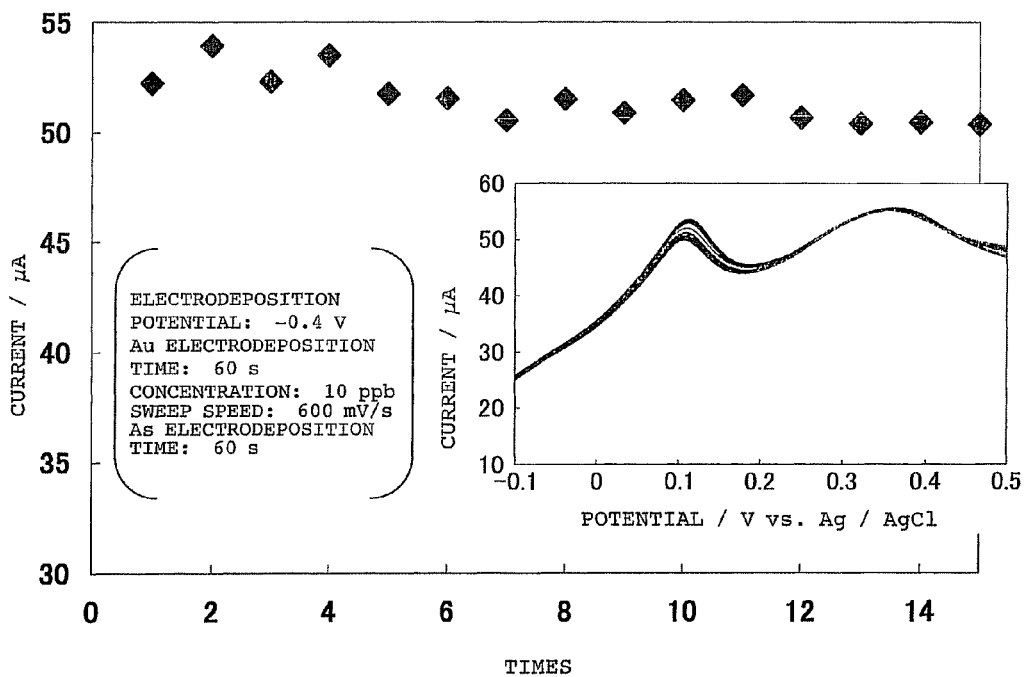
FIG. 14 shows the results of a test of the reproducibility of the analysis results of Embodiment 4.

The analysis conditions were the same as those given above, and the test was repeated 15 times, with the results shown in FIG. 14.

The test results are shown in the figure.

This figure shows that although the current value tends to decline somewhat as the test is repeated, a peak can still be reliably detected. Using a GC electrode on the other hand, the current value declines rapidly, and reproducibility is poor.

Embodiment 5

Measurement of As(V) Using a BDD-Au Electrode

Solutions containing As(V) at concentrations of 100 ppb, 300 ppb, 500 ppb, 800 ppb and 1000 ppb were analyzing under the following conditions using a BDD-Au electrode as the working electrode.

−1.5 V of negative potential was initially applied to the working electrode, and electrodeposition was then immediately performed with a potential of 0.4 V, after which the potential was swept in the positive direction.

| | |
|---|---|
| As electrodeposition potential: | −0.4 V |
| As electrodeposition time: | 60 s |
| Sweep speed: | 200 mV/s |
| Au electrodeposition time: | 1.0 min. |

Figure 15:
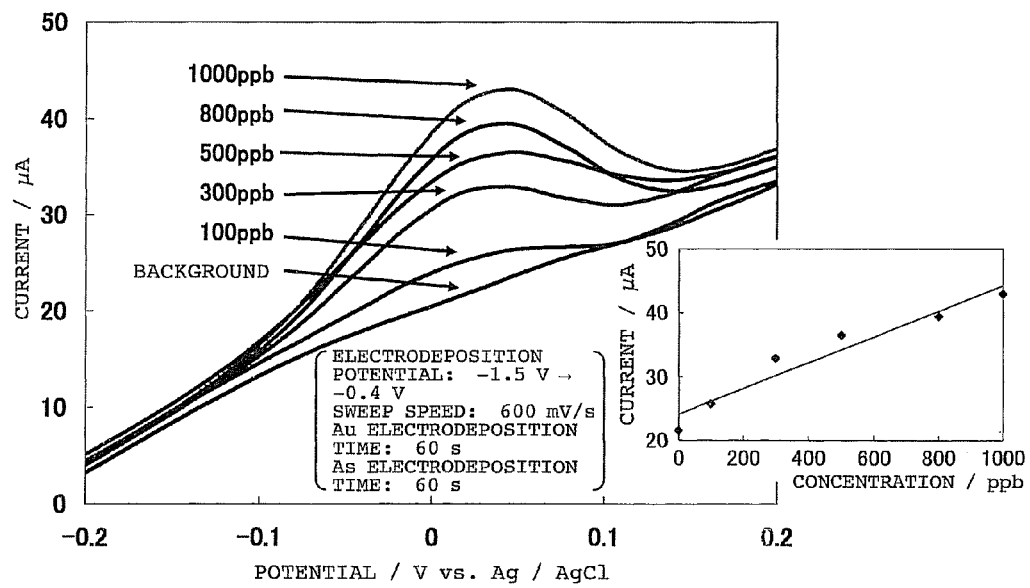
FIG. 15 shows the As solution analysis results obtained in Embodiment 5.

It can be seen from the results shown in FIG. 15 that peaks corresponding to concentrations of 100 to 1000 ppb can also be detected for As(V).

The results obtained from the analysis are shown in FIG. 15.

Embodiment 6

Measuring Total Amount of as(III) and as(V) Using a BDD-Au Electrode

A sample solution containing 1 ppm As(III) and 1 ppm As(V) was analyzed under the following measurement conditions.

−1.5 V of negative potential was initially applied to the working electrode, and electrodeposition was then immediately performed with a potential of −0.4 V, after which the potential was swept in the positive direction.

| | |
|---|---|
| As electrodeposition potential: | −0.4 V |
| As electrodeposition time: | 60 s |
| Sweep speed: | 600 mV/s |
| Au electrodeposition time: | 1.0 min |

An analysis was also performed in the same way with the same sample solution except that electrodeposition was performed with a potential of −0.4 V without first applying −1.5 V of negative potential to the working electrode, and the potential was then swept in the positive direction.

The analysis results obtained as described above are shown in FIG. 16. These analysis results are for As(III).

The analysis value for As(V) can then be obtained by subtracting the analysis value for As(III) from the analysis value for the combined amount of As(III) and As(V).

Embodiment 7

Measurement of Total Amount of As(III) and As(V) Using a BDD-Au Electrode

The following sample solutions (1) to (6) were prepared.
(1) As(III) 100 ppb+As(V) 1000 ppb
(2) As(III) 100 ppb+As(V) 800 ppb
(3) As(III) 100 ppb+As(V) 500 ppb
(4) As(III) 100 ppb+As(V) 300 ppb
(5) As(III) 100 ppb+As(V) 100 ppb
(6) As(V) 100 ppb These sample solutions were analyzed under the following conditions.

−1.5 V of negative potential was initially applied to the working electrode, and electrodeposition was then immediately performed with a potential of −0.4 V, after which the potential was swept in the positive direction.

Figure 16:
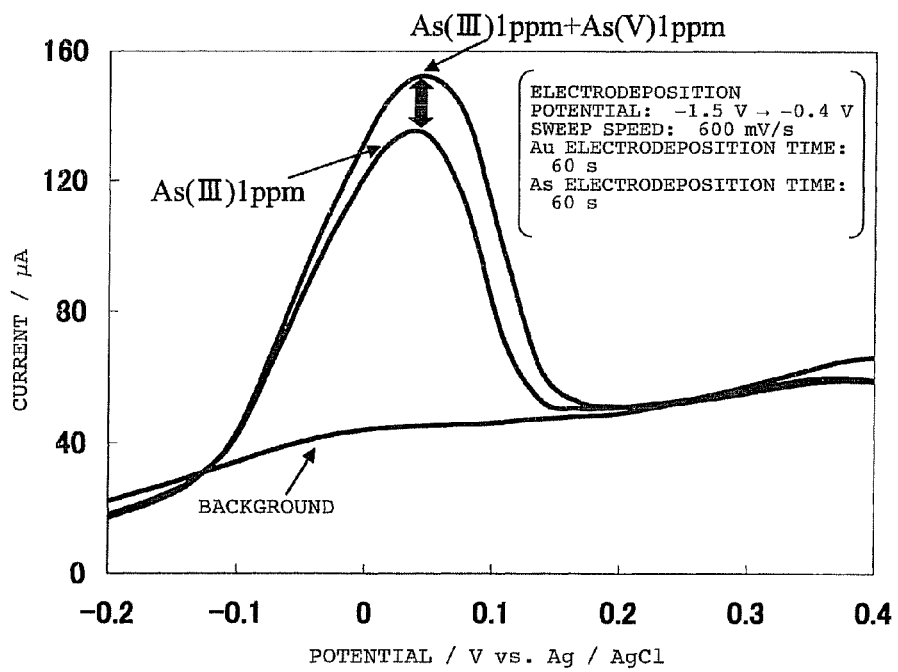
FIG. 16 shows the As solution analysis results obtained in Embodiment 6.

The analysis results are shown in FIG. 16. These analysis results are for the combined amount of As(III) and As(V).

| | |
|---|---|
| As electrodeposition potential: | −0.4 V |
| As electrodeposition time: | 60 s |
| Sweep speed: | 600 mV/s |
| Au electrodeposition time: | 1.0 min |

Figure 17:
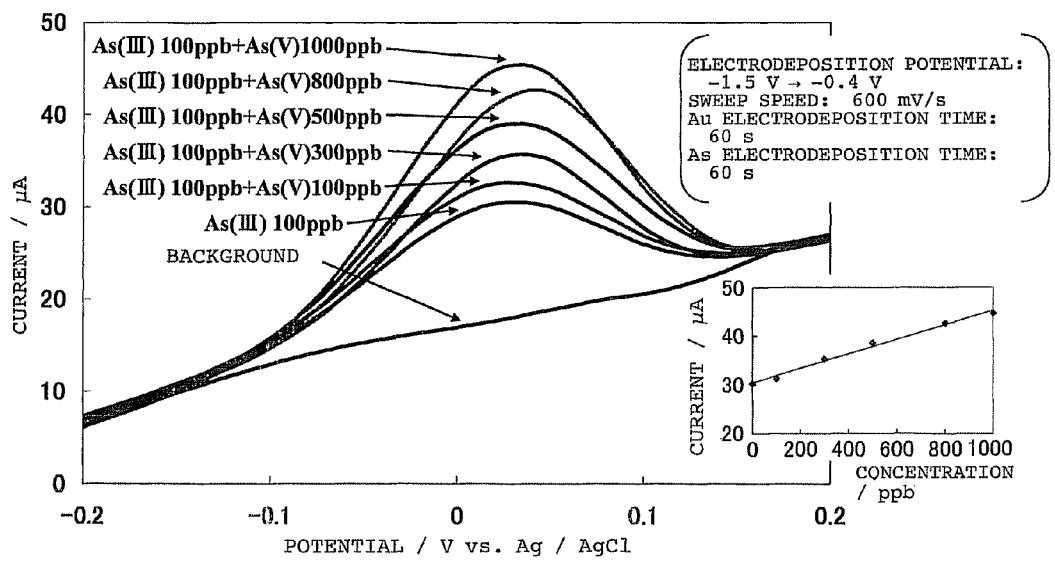
FIG. 17 shows the As solution analysis results obtained in Embodiment 7.

The analysis results are shown in FIG. 17. It can be seen from the results shown here that detection corresponding to the As(V) concentration can be achieved even in the presence of As(III).

[Other Testing]

Testing was performed to investigate whether other metal ions would interfere with arsenic analysis under the arsenic detection conditions.

Solutions of the following metals were prepared as test solutions. The concentrations are each about 10 times the environmental standards for those metals.

| | |
|---|---|
| Fe | 100 ppm |
| Pb | 10 ppm |
| Zn | 50 ppm |
| Mn | 100 ppm |
| Cr | 20 ppm |

Each solution was subjected to electrodeposition and elution operations under the following conditions.

Electrodeposition potential: −1.5→0.4 V

| | |
|---|---|
| Electrodeposition time: | 60 s |
| Sweep speed: | 200 mV/s |
| Au electrodeposition time: | 1.0 min |

Figure 18:
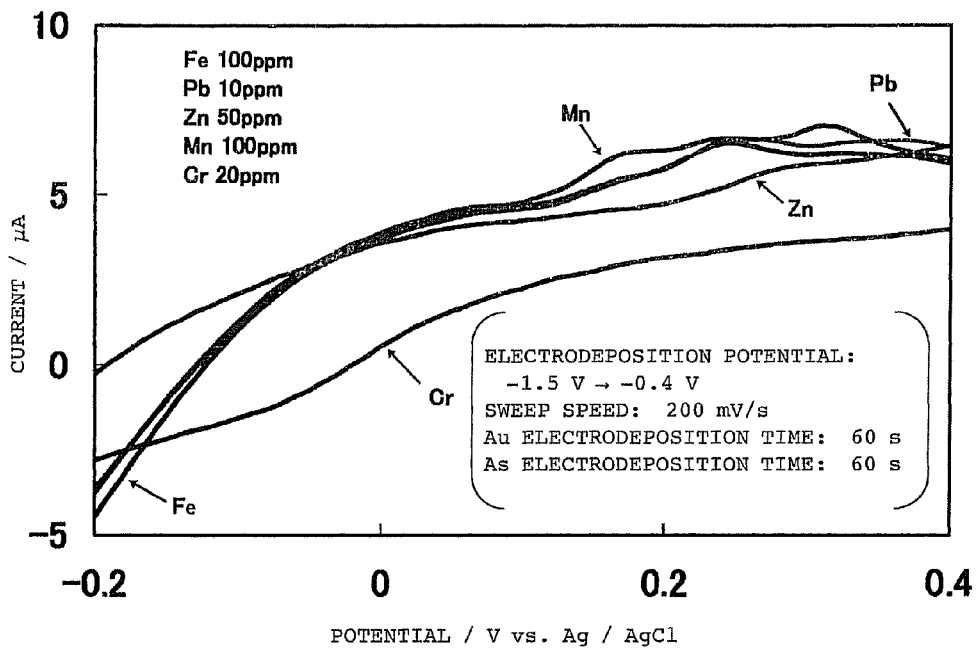
FIG. 18 shows analysis results obtained for metals other than As using the As detection conditions.

The results are shown in FIG. 18. As shown in FIG. 18, with these metals no peaks were observed near the peak potential of arsenic. This shows that arsenic analysis results will not be affected if these metals are present together with arsenic.

INDUSTRIAL APPLICABILITY

Because the present invention allows accurate analysis of a trace substance contained in a sample, it can be used favorably as a method for testing the quality of drinking water, waste water or the like.

What is claimed is:

1. An electrochemical analysis method comprising:

arranging a working electrode and a counter electrode in an electrolyte solution to be measured, wherein the working electrode is a boron-doped electroconductive diamond electrode and the electrolyte solution to be measured contains electrolytes including element (M1), which is a low-oxidation state of element (M) and electrolytes including element (M2) which is a high-oxidation state of element (M);

applying a negative potential to the working electrode so that the element (M2) is electrodeposited on a surface of the working electrode to cause an electrodeposition reaction and form an electrodeposit;

maintaining the potential of the working electrode at an electrodeposition potential of the element (M1), after the step of applying the negative potential; and sweeping the potential of the working electrode toward a positive potential, after the step of maintaining the potential of the working electrode, to thereby elute the electrodeposited element (M1), while detecting electric current changes in response to potential changes to thereby analyze a substance to be measured, the substance being dissolved as the element (M) of the electrolyte in the electrolyte solution to be measured.

2. An electrochemical analysis method according to claim 1, wherein the element (M) is arsenic (As), the element (M1) is As(III) and the element (M2) is As(V).

3. An electrochemical analysis method comprising:

arranging a working electrode and a counter electrode in an electrolyte solution to be measured that contains electrolytes including element (M1), which is a low-oxidation state of element (M) and element (M2), which is a high-oxidation state of element (M), wherein the working electrode is a boron-doped electroconductive diamond electrode;

applying a negative potential to the working electrode so that the electrolyte is electrodeposited on a surface of the working electrode to form an electrodeposit; and sweeping the potential of the working electrode toward a positive potential, after the step of applying the negative potential, to thereby elute the electrodeposit in the solution while detecting electric current changes in response to the potential changes to thereby analyze a substance to be measured which is dissolved as the electrolyte in the electrolyte solution to be measured, wherein the following analyses (1) and (2) are conducted on the electrolyte solution to be measured, the analysis value for the element (M2) being obtained from the analysis value for the element (M1) obtained by analysis (1) and the analysis value for the element (M) obtained by analysis (2):

(1) applying the negative potential to electrodeposit the element (M1) to the working electrode to thereby electrodeposit the element (M1) on the working electrode;

sweeping the potential toward a positive potential, after the step of applying the negative potential, to thereby elute the electrodeposited element (M1) while detecting electrical current changes in response to potential changes to thereby analyze the element (M1) which is dissolved as an electrolyte in the electrolyte solution to be measured, and (2) applying the negative potential to electrodeposit the element (M2) to the working electrode to thereby cause an electrodeposition reaction;

maintaining the potential of the working electrode at an electrodeposition potential of the element (M1), after the step of applying the negative potential;

sweeping the potential toward the positive potential to thereby elute the electrodeposited element (M1) while detecting electrical current changes in response to potential changes to thereby analyze the element (M) which is dissolved as an electrolyte in the electrolyte solution to be measured.

4. An electrochemical analysis method according to claim 3, wherein the element (M) is arsenic (As), the low-oxidation element (M1) is As(III) and the high-oxidation element (M2) is As(V).

* * * * *